(12) United States Patent
Larkins

(10) Patent No.: US 10,926,046 B1
(45) Date of Patent: Feb. 23, 2021

(54) GRAVITY DEPENDENT VENTILATOR

(71) Applicant: Grover L. Larkins, Miami, FL (US)

(72) Inventor: Grover L. Larkins, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/881,921

(22) Filed: May 22, 2020

Related U.S. Application Data

(60) Provisional application No. 63/003,633, filed on Apr. 1, 2020.

(51) Int. Cl.
*A61M 16/00* (2006.01)
*A61M 16/20* (2006.01)

(52) U.S. Cl.
CPC ...... *A61M 16/0063* (2014.02); *A61M 16/021* (2017.08); *A61M 16/206* (2014.02)

(58) Field of Classification Search
CPC .............. A61M 16/00; A61M 16/0057; A61M 16/006; A61M 16/0063; A61M 16/0072; A61M 16/0075; A61M 16/0081; A61M 16/20; A61M 16/206; A61M 16/208; A61M 16/209; A61M 2205/07; A61M 2205/073; A61M 2205/10; A61M 2205/103; A61M 1/1081; A61M 5/14216; A61M 5/145; A61M 5/1452; A61M 5/31576; A61M 2005/14533; F04B 5/00; F04B 5/02; F04B 9/04; F04B 9/042; F04B 9/045; F04B 17/03; F04B 35/01; F04B 35/04; F04B 39/0005; F04B 39/0016; F04B 53/12; F04B 31/00
USPC ....... 417/415, 328, 330–333, 254, 267, 522, 417/523, 525, 534; 128/204.21
See application file for complete search history.

(56) References Cited

U.S. PATENT DOCUMENTS

| | | | | |
|---|---|---|---|---|
| 1,893,670 A | * | 1/1933 | Goodner | A61M 16/0009 128/205.18 |
| 3,905,362 A | * | 9/1975 | Eyrick | A61M 16/0841 128/202.22 |
| 5,009,226 A | * | 4/1991 | Holt | A61M 16/0057 128/205.13 |
| 5,673,689 A | * | 10/1997 | Power | A61M 16/0057 128/203.12 |
| 6,789,540 B1 | * | 9/2004 | Lin | A61M 16/00 128/204.18 |

* cited by examiner

*Primary Examiner* — Rachel T Sippel
*Assistant Examiner* — Kelsey E Baller
(74) *Attorney, Agent, or Firm* — Saliwanchik, Lloyd & Eisenschenk

(57) ABSTRACT

A ventilator that utilizes a cam lever to raise a piston within a cylinder is provided. The weight of the piston can push breathable air out of the cylinder to a patient. A motor assembly provides the only electronic component necessary to operate the ventilator. Adjustments to volume, speed, and pressure can be made by adjusting mechanical components of the ventilator.

20 Claims, 17 Drawing Sheets

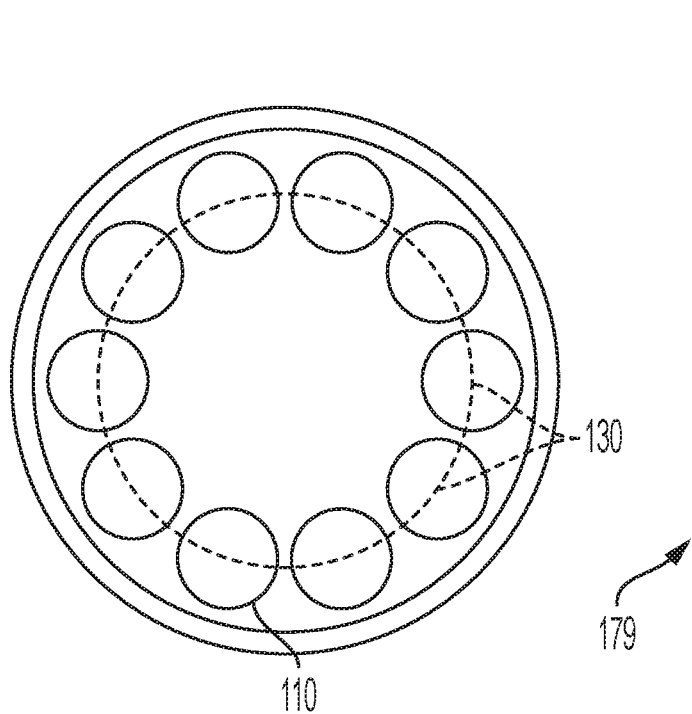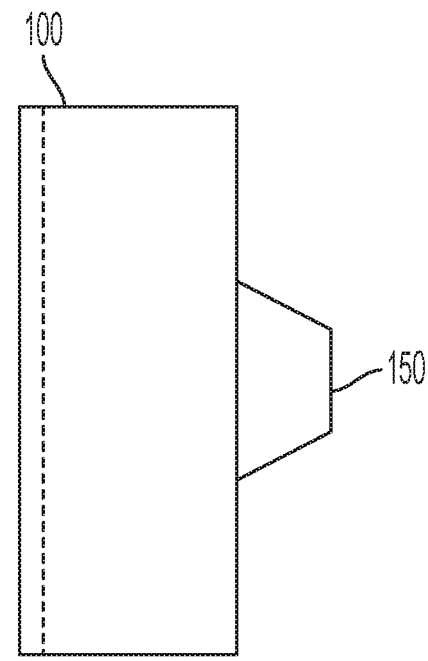
FIG. 17A  FIG. 17B
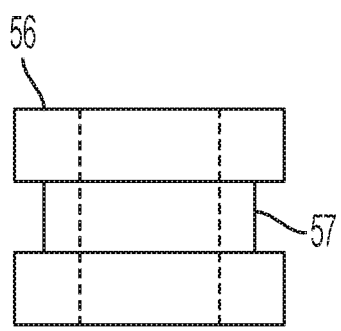
FIG. 18

GRAVITY DEPENDENT VENTILATOR

CROSS-REFERENCE TO RELATED APPLICATION

This application claims the benefit of U.S. Provisional Application Ser. No. 63/003,633, filed Apr. 1, 2020, which is hereby incorporated by reference herein in its entirety, including any figures, tables, and drawings.

BACKGROUND OF THE INVENTION

Ventilators help patients breathe by mechanically pumping and exhausting air from the lungs. Ventilators may be used to replace or supplement the patient's muscular effort normally used to inflate and deflate the lungs. Ventilators are often utilized to provide breathing assistance to patients suffering from diseases affecting the musculature required for breathing, such as muscular dystrophies, polio, amyotrophic lateral sclerosis (ALS), Guillain-Barre syndrome, and more recently COVID-19. Ventilators may also be used to assist conditions such as respiratory insufficiency or failure due to lung, neuromuscular, or musculoskeletal disease and diseases of respiratory control. Conditions related to sleep disordered breathing (SDB) (including mild obstructive sleep apnea (OSA)), allergy induced upper airway obstruction, viral infection of the upper airway and other non-disease-related breathing problems can also be assisted with a ventilator. Ventilators are also useful in providing breathing assistance to patients under sedation for surgical procedures and for patients suffering severe injuries, such as high spinal cord injuries and head traumas. In addition, a ventilator may also be configured to expand non-functioning regions of a patient's lung(s), such as collapsed alveoli.

Ventilators may function to supply a patient with clean breathable air (usually ambient air, with or without supplemental oxygen) at a therapeutic, a.k.a., ventilation, pressure(s) during appropriate times in the patient's breathing cycle. Pressure changes may be implemented in a synchronized fashion so as to permit greater pressures during inspiration and lower pressures during expiration.

The purpose of a ventilator is to supply breathable air to a patient. Ventilators conventionally are mechanically complex devices that require highly trained persons to, build, service, and function. Within the housing of a typical ventilator are a number of tubes to connect mechanical and electrical valves and sensors used to control and measure the characteristics of ventilation. A considerable amount of time, expertise, and specialized equipment is necessary to manufacture typical ventilators in use today.

One type of ventilator is the bag-valve-mask (BVM) ventilator, which is less complicated than other ventilators, but has a very limited lifespan. Sometimes referred to as an "AMBU bag", these types of ventilators often will be unusable after about one day, assuming 30 compressions per minute for 43,000 cycles in a 24 hour period. BVM ventilators also do not deliver a metered volume, nor do they provide a constant pressure. They are typically bulky because their construction. A BVM ventilator requires about 0.25 cubic feet to store/ship, so if there are 10,000 patients that require assistance with breathing for about 10 days (assuming each patient needs a new bag each day), 100,000 bags, comprising 25,000 cubic feet of storage space, need to be transported every day.

While precision in ventilator design and operation can be important, the most important function is keeping a patient alive by assisting with breathing. The recent coronavirus (COVID-19) crisis has highlighted the need for a ventilator that is capable of assisting a patient with breathing, while also being easy to produce, rugged, and able to be manufactured and/or operated without requiring a significant amount of technical expertise. More importantly, there is a need for a ventilator that can be manufactured quickly and with easily accessible components.

BRIEF SUMMARY OF THE INVENTION

Embodiments of the subject invention provide gravity-dependent and/or gravity-assisted ventilators for breathing assistance, and methods of manufacturing and using the same. The ventilator can employ a simple, easily-sourced motor as the sole electrical component. All other components of the ventilator can be passive. Advantageously, the ventilators of embodiments of the subject invention are robust, durable, and essentially fail-safe. Further, the ventilator design inhibits over-insufflation of a patient's lungs while delivering a repeatable volume of breathable air. The pressure of the breathable air delivered to a patient can be well regulated and adjustable.

Conventional ventilators utilize an array of electrical components to operate, control, and regulate the volume of breathable air and the intervals at which it is delivered to a patient. The complexity of conventional ventilators and their dependence on specific electronic components makes them vulnerable to failure. In the event of a situation where modern electronics will not function (e.g., EMP, Solar Flare, obsolescence) ventilator of embodiments of the subject invention can continue to function reliably and repeatably. Advantageously, in situations where insufficient ventilators are available to meet patients' needs (developing nations, pandemics, natural disasters, war) ventilators of embodiments of the subject invention can be rapidly produced with easily accessible components, by local and relatively unskilled labor without the need for a high level of technological support.

Advantageously, the ventilators of embodiments of the subject invention can utilize gravity to regulate the pressure of the breathable gas provided to a patient. In a specific embodiment, a weighted piston in a chamber is used to generate a constant gas pressure in a lower portion of the ventilator. The piston is raised or drawn up by a cam lever operated with a motor operably connected to a cam lever that turns on the motor shaft. Rotation of the cam lever raises the piston. Further, an upper portion of the chamber, above the piston, can be used to take in the breathable air, usually ambient air, for the each cycle and can also serve as a mixing chamber when additional gas, such as oxygen, is mixed with the breathable air.

A passive valve can be used to inhibit excessive pressure build-up in an upper portion of the chamber. Another passive valve can be used to regulate the passage of breathable air from the upper portion through the piston to the lower portion of the chamber. Additionally, the volume of breathable air can be adjusted by the location of a crank pin on the cam lever. The crank pin can be offset from an axis of rotation of the cam lever, which is rotated by the motor. The crank pin is connected to the piston by a flexible or semi-flexible draw cable. Rotation of the cam lever raises the cam pin, which raises the cable attached to the piston. When the crank pin reaches a certain point, the cam lever "falls", releasing the cable and allowing the piston to free-fall in the chamber, forcing the air in the lower portion towards the patient.

In an embodiment, a ventilator can comprise: a chamber having a closed bottom, a sidewall, a top opposite from the bottom in an axial direction; a cap covering the top of the chamber; a piston disposed in an interior of the chamber, in contact (e.g., direct, physical) with the sidewall of the chamber, and dividing the interior of the chamber into an upper portion between the piston and the cap and a lower portion between the piston and the bottom of the chamber; an inlet configured to provide air into the upper portion of the chamber; an outlet configured to evacuate air from the bottom portion of the chamber; and a driving element operably connected to the piston and configured to move the piston upwards towards the top of the chamber in the axial direction. The piston can comprise at least one piston channel therethrough, and the piston can further comprise a passive piston valve on the at least one piston channel and configured to allow air to flow through the at least one piston channel from the upper portion of the chamber to the lower portion of the chamber while inhibiting air from flowing through the at least one piston channel from the lower portion of the chamber to the upper portion of the chamber. The cap can comprise at least one vent therethrough, and the cap further can comprise a passive cap valve on the at least one vent and configured to allow air to flow through the at least one vent from the upper portion of the chamber to an outside of the chamber while inhibiting air from flowing through the at least one vent from the outside of the chamber to the upper portion of the chamber. The driving element comprises a motor, and the piston has a mass that is large enough such that the piston, when not being moved upwards or inhibited from moving downwards by the driving element, overcomes friction with the sidewall of the chamber and pressure from the air in the lower portion of the chamber to move (i.e., fall) downwards towards the bottom of the chamber due to gravity. The passive piston valve can comprise a first membrane on a bottom face of the piston that faces the bottom of the chamber, and the passive cap valve can comprise a second membrane on either a top face of the cap that faces the outside of the chamber or a bottom face of the cap that faces the piston. The motor can comprise a motor shaft and a motor element configured to rotate the motor shaft, and the driving element can further comprise: a cam lever connected to the motor shaft; a cam pin connected to the cam lever; and a draw cable connected to the cam pin and the piston; the driving element being configured to move the piston upwards by a turning of the cam lever together with the rotating of the motor shaft, causing the cam pin to move upwards and pull the piston upwards via the draw cable; and the driving element allowing the piston to move downwards due to gravity when the cam pin is not moving upwards. The driving element can further comprise a cam lever step connected to the cam lever and a motor shaft pin on the motor shaft, and the motor shaft pin can be configured to engage the cam lever step as the motor shaft rotates, causing the cam lever to turn together with the motor shaft. The cam lever can comprise a plurality of adjustment bores at different distances from the motor shaft, and each configured to receive the cam pin. The chamber can be a cylinder; the piston can have a circular cross-section, taken in a horizontal direction perpendicular to the axial direction; and the cap can have a circular cross-section taken in the horizontal direction. The piston can have a variable radius through its thickness, such that an uppermost portion of the piston and a lowermost portion of the piston are in contact with the sidewall of the chamber while an intermediate portion of the piston between the uppermost portion and the lowermost portion is spaced apart from the sidewall of the chamber. The motor can be an electric motor, and the motor can be the only electric element of the ventilator or in operable communication with the ventilator. The ventilator can further comprise: a shuttle valve connected to the outlet and configured to alternate air evacuated via the outlet between two different patients connected to the ventilator; a first pressure sensor connected to the inlet; a second pressure sensor connected to the outlet; and/or a photomicrosensor disposed on the cap (e.g., mounted in a depression in the cap facing the piston) and configured to measure a distance between the cap and the piston.

In another embodiment, a method of providing ventilation to a patient in need of ventilation can comprise: providing a ventilator as described herein; connecting the outlet to the patient; providing breathable air to the upper portion of the chamber via the inlet; and operating the motor so that the piston is cyclically and repeatedly pulled upwards and then allowed to fall downwards due to its mass, forcing air from the upper portion of the chamber to the lower portion of the chamber through the at least one piston channel during the upwards movement and pushing air out of the lower portion via the outlet and to the patient during the downwards falling.

In another embodiment, a gravity-assisted ventilator can comprise: a chamber; an input port coupled to the chamber; an output port coupled to the chamber; a weighted piston movably located in the chamber between the input port and the output port, the weighted piston including a top surface, a bottom surface, and at least one cavity passing through the weighted piston from the top surface to the bottom surface creating a piston channel; a passive valve coupled to the bottom surface of the weighted piston; and a motor mechanically coupled to the weighted piston allowing for the weighted piston to be lifted and dropped within the chamber between the input port and the output port. The weighted piston can divide an interior of the chamber into an upper cavity and a lower cavity. The ventilator can be configured such that the top surface of the weighted piston and the bottom surface of the weighted piston are both perpendicular to a gravity direction (i.e., both are horizontal), and the weighted piston drops within the chamber with assistance of gravity. The ventilator can be further configured such that as the weighted piston drops it causes a volume of air in the lower cavity to evacuate out of the output port. The volume of air evacuated out of the outlet port is proportional to how much air is in the lower cavity before the weighted piston drops.

BRIEF DESCRIPTION OF THE DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description are specific to the embodiments disclosed. Any variations of these dimensions that will allow embodiments of the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 12A illustrates a shuttle valve and FIG. 12B illustrates an embodiment of a captive piston with a magnet.

FIGS. 17A and 17B illustrate an embodiment of a piston, according to the subject invention. FIG. 17A shows a top plan view of a piston with the channels. FIG. 17B shows a side elevation view with a seat for supporting a weight.

FIG. 18 shows an embodiment of a nipple, according to subject invention, to which a bladder can be attached within a chamber.

DETAILED DESCRIPTION OF THE INVENTION

Figure 1:
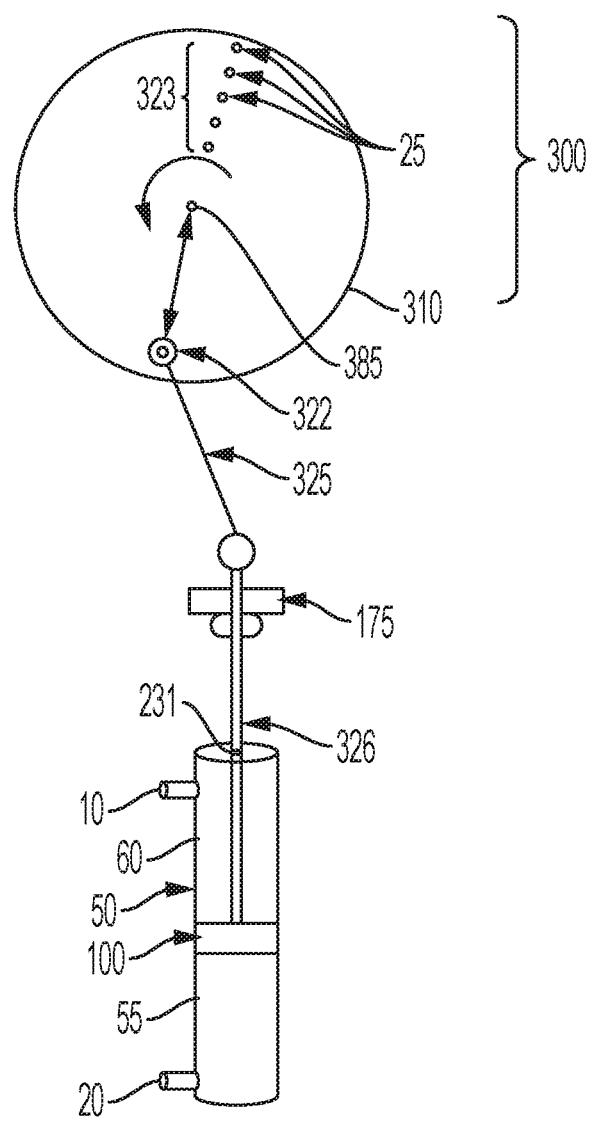
FIG. 1 shows an embodiment of a ventilator, according to the subject invention. In this embodiment, the cable is attached to a draw rod that raises and lowers the piston.

Embodiments of the subject invention provide gravity-dependent and/or gravity-assisted ventilators for breathing assistance, and methods of manufacturing and using the same. The ventilator can employ a simple, easily-sourced motor as the sole electrical component. All other components of the ventilator can be passive. Advantageously, the ventilators of embodiments of the subject invention are robust, durable, and essentially fail-safe. Further, the ventilator design inhibits over-insufflation of a patient's lungs while delivering a repeatable volume of breathable air. The pressure of the breathable air delivered to a patient can be well regulated and adjustable.

Embodiments provide ventilators for supplying breathable air to a patient in need of breathing assistance. The ventilator embodiments employ a gravity-dependent (or gravity-regulated) apparatus that requires simple, easily-sourced, components operated with a motor; the motor can be the sole electrical component, though embodiments are not limited thereto. Gravity can be used to regulate the pressure of the breathable air transmitted to a patient by the use of a simple weighted piston in a chamber to generate a constant gas pressure. The "weighted piston" does not need to have a weighted object (or separate weight) attached and must just have enough mass to cause the volume of air/oxygen in the lower portion/cavity of the chamber to be pushed out of the outlet of the chamber (e.g., pushed out to a patient). In some embodiments, the weighted piston does have one more weighted objects (or separate weights) attached (though as mentioned this is not necessary).

Advantageously, ventilators of embodiments of the subject invention are robust, durable, and less prone to failure than conventional ventilators. Further, the ventilators of embodiments of the subject invention have mechanisms that inhibit over-insufflation of a patient's lungs by breathable air. The ventilator can deliver an adjustable and repeatable volume of breathable air that can be easily adjusted to different pressures.

Embodiments of the subject invention are particularly suited for use in situations where numerous ventilators are required to be quickly manufactured. The components of a ventilator of embodiments of the subject invention can usually be sourced locally and assembled without extensive expertise or training. Thus, in situations where multiple patients are in need of immediate breathing assistance, the ventilators of embodiments of the subject invention can be manufactured easily and quickly and can provide dependable, repeatable use.

In the description that follows, a number of terms are utilized. In order to provide a clear and consistent understanding of the specification and claims, including the scope to be given such terms, the following definitions are provided.

The term "patient" as used herein, describes an animal, including mammals (e.g., humans), to which the devices and methods of the present invention can be applied and that can benefit from such application.

As used herein, the terms "about" or "approximately" mean at least close to a given value or either end of a range as is necessary to cover manufacturing variances, equipment tolerances, and normal variances in material, as understood by those skilled in the art. When used with a numerical value, "about" means within 5% of the numerical value.

As used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

Figure 23:
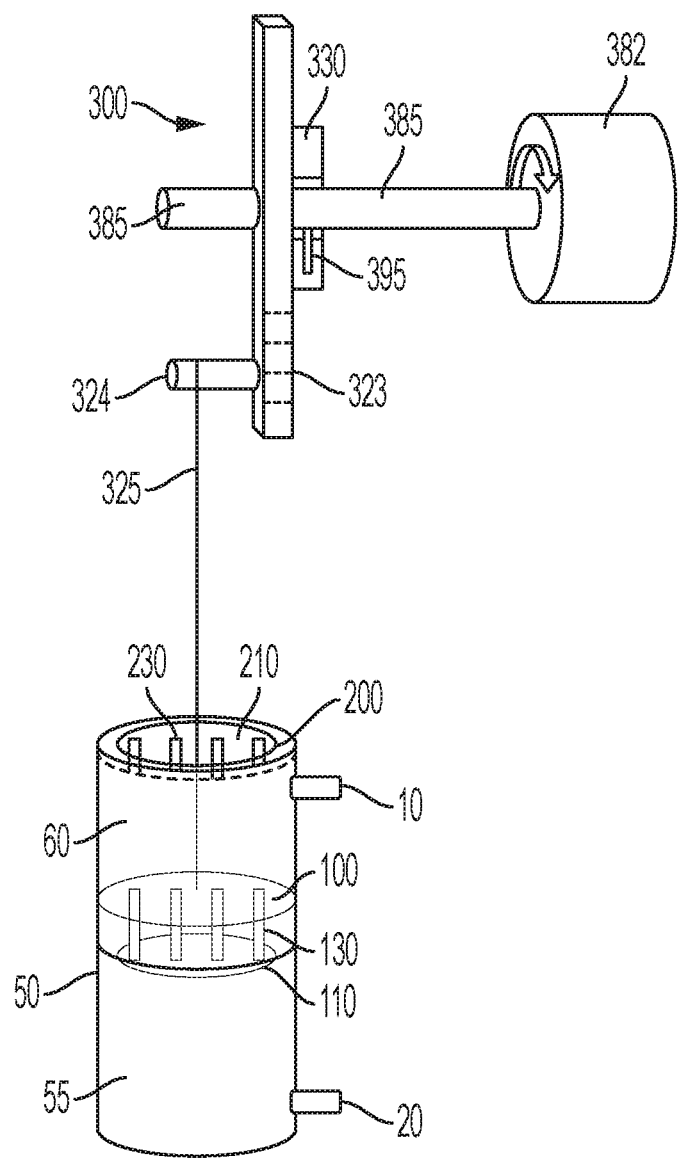
FIG. 23 is schematic view of a ventilator that utilizes a weighted piston, according to an embodiment of the subject invention.

Reference will be made to the attached figures on which the same reference numerals are used throughout to indicate the same or similar components. Referring to FIG. 23, which shows a ventilator of an embodiment of the subject invention, a chamber 50 contains a slidable piston 100 that separates the chamber into an upper portion 60 (can also be referred to as an upper cavity) of the chamber and a lower portion 55 (can also be referred to as a lower cavity) of the chamber. The piston can have a plurality of channels 130 therethrough that open onto the upper portion and the lower portion. At the bottom end of the piston there can be a passive piston valve 110 that can open and close the channels. For example, the passive piston valve 110 can be configured such that it opens when the piston slides up towards the upper portion 60 (thereby allowing air from the upper portion 60 to enter the lower portion 55) and closes when the piston slides down towards the lower portion 55 (thereby pushing air out of the lower portion 55 through the outlet 20. The top of the chamber can be closed by a cap 200 that has a plurality of vents 230 between the upper portion 60 and the outside of the chamber 50. The top of the cap 200 can also have a passive cap valve 210 that covers the vents. The piston 100 can be raised within the chamber by a draw cable 325 that attaches to the piston 100, goes through the cap 200, and operably attaches to a cam lever 300. The draw cable 325 can be attached to the cam lever 300 with, for example, a cam pin 324. The cam lever 300 can have multiple adjustment bores or apertures 323 for receiving the cam pin 324. The adjustment bores/apertures 323 can be created by any suitable method (e.g., drilling, casting, molding, etc.). The height to which the piston 100 is raised in the chamber 50 can be adjusted by the position of the cam pin 324 on the cam lever 300. The cam lever 300 can also include a step 330 utilized to rotate the cam lever 300 until the cam pin 324 is at least 180° from a biased position below the motor shaft 385. The cam lever 300 is rotated by a motor assembly that includes a motor 382 and a motor shaft 385. The motor shaft 385 can have a step pin 395 that temporarily engages with the step 330 on the cam lever 300 as the motor shaft 385 is rotated.

The ventilator 5 can operate by moving breathable air taken into the upper portion 60 to the lower portion 55 so that it can be forced out of the lower portion 55 via the outlet 20 to a patient by a weighted piston 100. In one embodiment, the weighted piston can be made from a metal material, such as a heavy metal material; in alternative embodiments, the weighted piston can be molded from approved (e.g., FDA approved) plastic(s) and filled inside with a heavier material (e.g., metal such as heavy metal, or other heavy material). The "weighted piston" does not need to have a weighted object (or separate weight) attached and must just have enough mass to cause the volume of air/oxygen in the lower portion/cavity of the chamber to be pushed out of the outlet of the chamber (e.g., pushed out to a patient). In some embodiments, the weighted piston does have one more weighted objects (or separate weights) attached (though as mentioned this is not necessary).

The ventilator utilizes the motor 382 to turn the motor shaft 385, which rotates the cam lever 300 and the cam pin 324 thereon. Initially, the weight of the piston can bias the cam lever with the cam pin below the motor shaft, as shown in FIG. 23. The initial position of the piston in the chamber can be adjusted by the positioning the cam pin in the appropriate adjustment bore 323 on the cam lever. The position of the piston in the chamber can determine the volume of breathable air in the lower portion 55, which will be provided to a patient. As the motor shaft rotates, the step pin 395 rotates until it contacts the bottom 332 of the step 330 on the cam lever 300, which causes the entire cam lever 300 to rotate around the motor shaft. This simultaneously raises the piston 100 in the chamber 50. As the piston is raised on the draw cable 325, breathable air that was pumped into the upper portion 60 (via the inlet 100) is forced through the channels 130 in the piston, which simultaneously causes the passive piston valve 110 to open, so as to fill the lower portion 55 with the breathable air. The passive cap valve 210 can open if necessary to inhibit the upper portion from being over pressurized. When the step pin 395 rotates the bottom of the step 330 to the top of the motor shaft 385, the weight of the piston 100 can cause the cam lever 300 to rotate more quickly or "fall" back to the biased position with the cam pin 324 below the motor shaft 385. This sudden drop causes the weighted piston 110 to be released in the chamber 50. The volume of breathable air that was drawn into the lower portion 55 through the channels 130 is pressurized by the weighted piston 100 thereon, which causes the passive piston valve 110 to close and forces the breathable air out of the lower portion 55 (via the outlet 20) to a patient at a constant pressure. As the piston 100 is descending in the lower portion 55, forcing the breathable air out, the upper portion 60 is refilling with breathable air (via the inlet 10) and the motor shaft 385 is rotating around until it engages with the bottom of the step 330 to rotate the cam lever 300. As the piston 100 is raised, the breathable air is forced into the lower portion 55 and when the piston 100 falls, the volume of breathable air in the lower portion 55 is forced out the outlet 20 to the patient. This process is repeated as long as the ventilator 5 is operating.

Though the chamber 50 is depicted as a cylinder in the figures, this is for exemplary purposes and should not be construed as limiting. Other shapes of the chamber can be used (e.g., square or rectangle cross-section (parallelepiped), triangular cross-section), so long as the piston is in contact with the sidewall(s) of the chamber. The chamber can also be made from any suitable material (e.g., steel, aluminum, plastic, other FDA-approved material(s)). In many embodiments, the piston 100 slides in the chamber with the sidewall(s) providing a slidable mechanical contact fit.

Though the piston channels 130 are depicted as having a circular cross-section, this is for exemplary purposes only and should not be constructed as limiting. The piston channels can have any suitable shape (e.g., square cross-section, rectangular cross-section, triangular cross-section, other polygonal cross-section, or irregular cross-section).

In certain embodiments, the breathable air forced out of the chamber can be alternated between two patients with a shuttle valve 600. Various types of sensors 500 can also be utilized with embodiments to monitor the position of the piston and the breathable air pressure. Each of these general components can have one or more sub-components, which will be discussed in detail below.

In embodiments, the ventilator 5 can employ a rigid chamber 50 for containing and supplying breathable air to a patient. The chamber can be divided into two general portions: a lower portion 55; and an upper portion 60. The chamber is divided by a piston 100 that traverses up and down within the chamber as the breathable air is taken in and pushed out of the chamber. FIGS. 1, 2, 4, 8A, and 10B show non-limiting embodiments of chambers 50 that can be used with embodiments of the subject invention.

Figure 2:
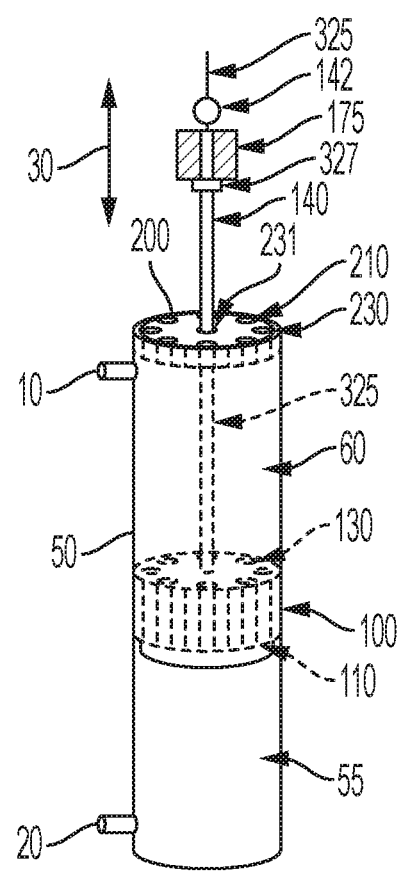
FIG. 2 shows an embodiment of certain internal components of a ventilator, according to the subject invention.
Figure 7A:
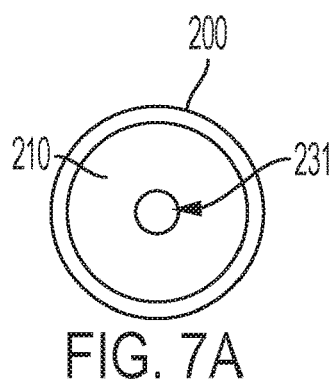
FIG. 7A illustrates a top view of an embodiment of a cap that can be positioned at the top of the chamber to close the chamber. The cap can include a clearance aperture through which the cable traverses to the piston.
Figure 7B:
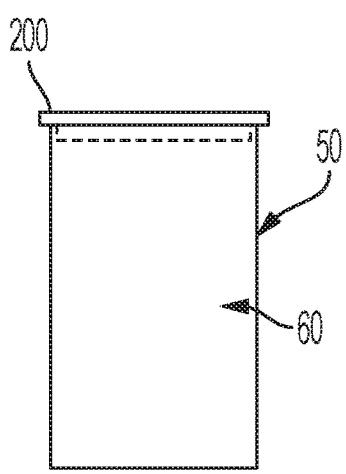
FIG. 7B show an embodiment of the upper portion in a chamber with the cap, shown in FIG. 7A, arranged thereon.
Figure 7C:
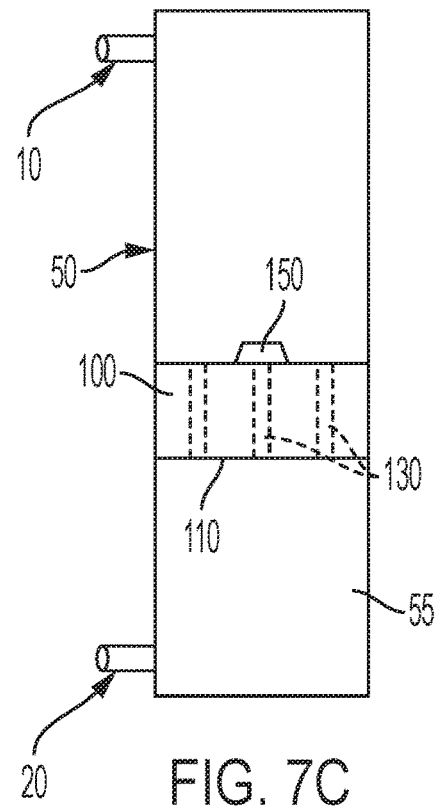
FIG. 7C shows an embodiment of a cylindrical chamber, according to the subject invention, with a piston therein.

In one embodiment, breathable air is taken into the upper portion 60 through an intake tube 10. Breathable air is pushed out from the lower portion 55 through an outlet tube 20 that leads to a patient mask. The demarcation between these two chambers is determined by the position of the slidable piston 100 within the chamber. FIGS. 1 and 2 show examples of an inlet 10 and outlet 20 tube arranged on a chamber 50. FIGS. 7B and 7C illustrate examples of an upper portion 60 and lower portion 55 and a piston 100 arranged therein. In one embodiment, the inlet tube supplies breathable air from the ambient environment. In a further embodiment, the inlet tube is operably attached to an alternative gas supply, such as, for example, oxygen, that takes the place of or is mixed with the breathable air to a patient. In yet a further embodiment, a humidifier is operably connected to the inlet tube (e.g., in addition to an oxygen supply). The ambient air and any other gas or moisture that may be supplied therewith can be mixed in the upper portion as it is taken in by the force of the piston and further mixed as the breathable air and gas are forced into the lower portion. Thus, the breathable air supplied to a patient can be from the ambient environment, one or more gas source(s), a humidifier, or some combination thereof.

Figure 6A:
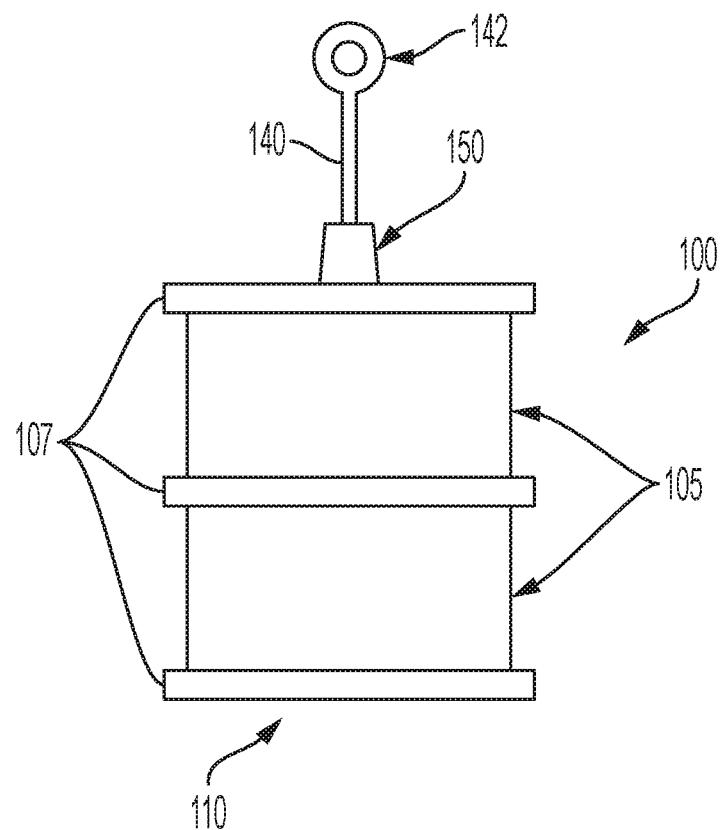
FIG. 6A illustrates an embodiment of a piston, according to the subject invention. In this embodiment, a weight support is shown in the top of the piston and a cable rod extends from the top of the piston for attachment to a cable.

The unique advantage of the ventilators of embodiments of the subject invention is the use of a piston 100 slidably arranged in the chamber 50 that functions to move the breathable air out of the chamber to the patient by gravity-dependent compression force. In one embodiment, a piston has an outer shape that fits within the chamber so as to maintain the piston in a vertical alignment within the chamber. FIG. 17B illustrates an example of a piston that can be slidably arranged in a chamber. In one embodiment, the weight of the piston divided by the cross-sectional area of the chamber 50 determines the pressure output to the patient. Stated another way, the mass of the piston multiplied by the gravitational acceleration determines the pressure of the breathable air supplied to a patient through the outlet tube 20. To facilitate the sliding motion of the piston within the chamber, it can be beneficial to reduce the frictional force between the piston and the chamber. FIG. 6A shows a side view of a non-limiting embodiment of a piston having one or more sub-diameter or indented sections 105 that do not contact the chamber, which can reduce the frictional forces. Two or more clearance diameter sections 107 above and below the indented sections can slidably contact the chamber to maintain the vertical orientation of the piston.

Figure 6B:
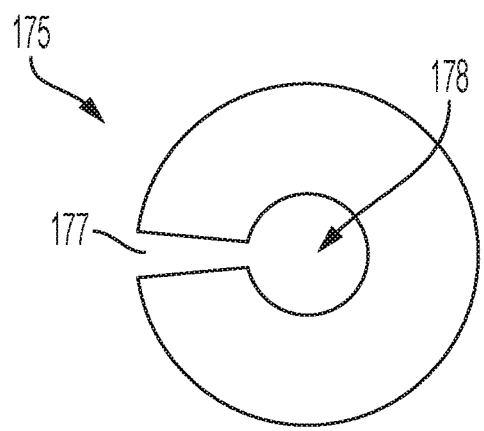
FIG. 6B illustrates an embodiment of a weight that can be positioned on a piston, according to the subject invention.

To adjust the pressure of the breathable air supplied to a patient, the compression force applied to the breathable air in the lower portion can be changed. In one embodiment, the piston 100 can be changed to provide a lighter or heavier piston, as the need dictates. Alternatively, one or more weights 175 can be added to the piston to change the downward force. FIG. 6B illustrates one example of a weight that can be added to the top of a piston in the chamber to change the downward force applied to the breathable air in the lower portion. As discussed below, the weight can have a slot 177 to accommodate the piston attachment to the cam lever or the cable 325. It can also be important to ensure that the weight does not tilt, slide, bind, or otherwise disengage from the piston. In one embodiment, the piston has a stand 150 on which the weight is supported and held in place. In a further embodiment, the stand is conical or frustoconical in shape and the weight has a central, tapered seat 178, congruent with the slot, that fits or interdigitates with the stand to maintain the weight in a upright position on the stand.

Breathable air in the upper portion 60 is moved into the lower portion 55 through multiple channels 130 that extend from the top to the bottom of the piston 100. When the piston is drawn towards the top of the chamber, breathable air taken into the upper portion 60 through the intake tube 10 is forced through the channels. FIGS. 1, 2, 3, and 17A show examples of multiple channels in a piston.

Figure 3:
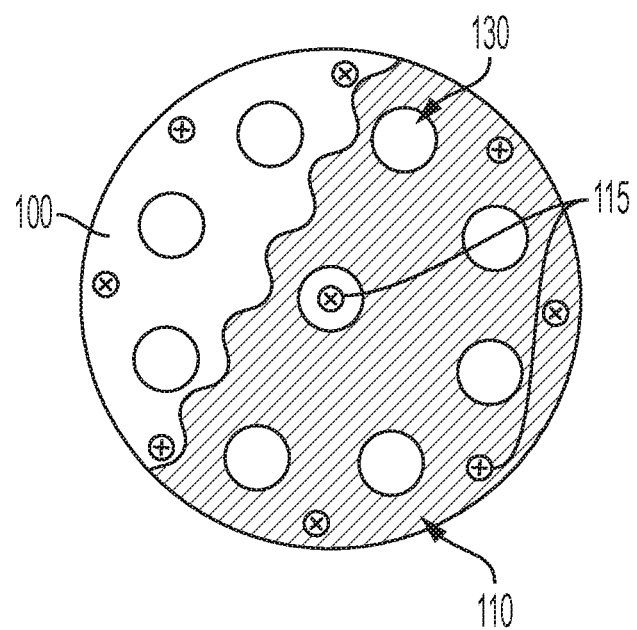
FIG. 3 is a bottom view of an embodiment of a piston with a first valve (partial) arranged over the channels in the piston.

To inhibit some or all of the breathable air from being forced back into the upper portion 60 when the weight of piston is applied to the breathable air in the lower portion, there can be a valve on the piston. One or more one-way piston valves 110 can be arranged on the bottom of the piston and removably covers the multiple channels 130 where they open into the lower portion. The one-way piston valve allows the breathable air to move into the lower portion, but inhibits the breathable air in the lower portion from moving into the upper portion. In a more specific embodiment, the one-way valve is passive, such that it controlled by the movement of the breathable air in the chamber. Examples of passive, one-way valves that can be utilized on a piston, include, but are not limited to, a flapper valve, a reed valve, or other flexural membrane or disk. For example, the piston can have a membrane on a bottom face thereof (facing the lower portion 55 of the chamber) that functions as a passive piston valve. FIGS. 2, 3, and 7C illustrate examples of a piston valve 110 arranged on the bottom of a piston. There can also be a recess 179 in the bottom of the piston in which the one-way valve can be positioned. This is not shown in the Figures, but would be understood by a person of skill in the art.

Over-pressurization of the upper portion 60 can inhibit the movement of the piston 100, over-pressurize the lower portion 55, impair the operation of the piston valve 110, and/or, in extreme cases, damage the ventilator 5. In one embodiment, the chamber has a cap 200 that closes the top of the chamber, such as shown in, for example, FIGS. 2 and 7A. The cap can be removable and allow access to the interior of the chamber. In one embodiment, the cap has multiple vents 230 through the cap that allow excess breathable air in the upper portion to escape to the ambient environment.

To inhibit air from the ambient environment entering the upper portion 60, there can be a valve on the cap 200. In one embodiment, a one-way cap valve 210 is arranged on the top of the cap and removably covers the multiple vents 230 where they open onto the top of the cap. The one-way cap valve allows the breathable air to escape from the upper portion 60 in the event of over-pressurization, but inhibits air in the ambient environment from moving into the upper portion. In a more specific embodiment, the one-way valve is passive, such that it controlled by the movement of the breathable air in the upper portion 60. Examples of passive, one-way valves that can be utilized on a cap, include, but are not limited to, a flapper valve, a reed valve, or other flexural membrane or disk. For example, the cap can have a membrane on a top face (facing away from the chamber 50) or a bottom face (facing the chamber 50 interior) thereof that functions as a passive valve; in one embodiment of the ventilator, a first such membrane is disposed on a bottom face of the piston, and a second such membrane is disposed on the top face or the bottom face of the cap. FIGS. 2 and 7A illustrate examples of a cap valve 110 arranged over the vents 230 on the top of a cap.

The piston 100 is drawn upwards and allowed to free fall within the chamber to compress the breathable air in the lower portion, forcing it out of the outlet tube 20 and to the ventilation mask of a patient. In a particular embodiment, the piston is drawn up at a regular interval so that the weight of the piston, when allowed to free fall, compresses the air drawn into the lower portion at a likewise regular interval. Ideally, the interval is adjustable to individual patients. In one embodiment, the piston is operably attached to and is drawn up by a motor. In a specific embodiment, the motor is an electric motor with a motor shaft 385. In many embodiments, the electric motor is the only powered component utilized with the ventilator.

Figure 9:
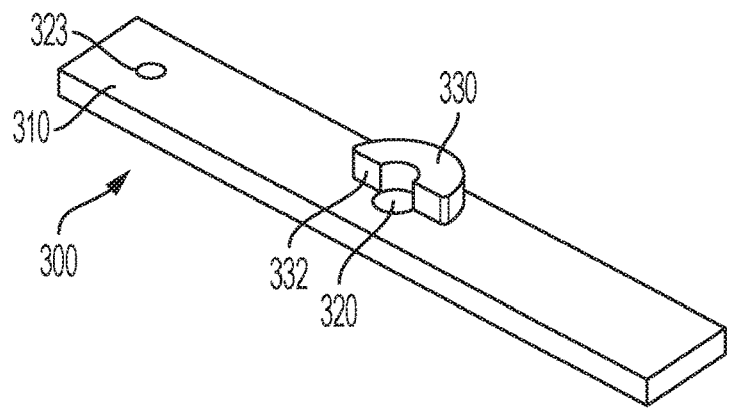
FIG. 9 is an illustration of an embodiment of a cam lever, according to the subject invention. The step that engages with the pin on the motor assembly shaft can be seen on the rotating lever.

Attached to the motor shaft 385 is a cam lever 300, such as shown in, for example, FIGS. 1 and 9. The cam lever can rotate freely on the motor shaft. The cam lever can be attached to the motor shaft to operate as a type of simple lever to draw the piston up to a pre-determined height, after which it then freely rotates to drop or release the piston. In one embodiment, a flexible or semi-flexible draw cable attaches at or about a center of the piston. If a stand 150 (described above) is utilized on the piston the draw cable can extend therefrom and a weight 175 can be arranged around the draw cable 325 through the slot 177, as shown in, for example, FIGS. 2, 6A and 6B. The draw cable 325 can be attached to the cam lever 300.

Figure 5:
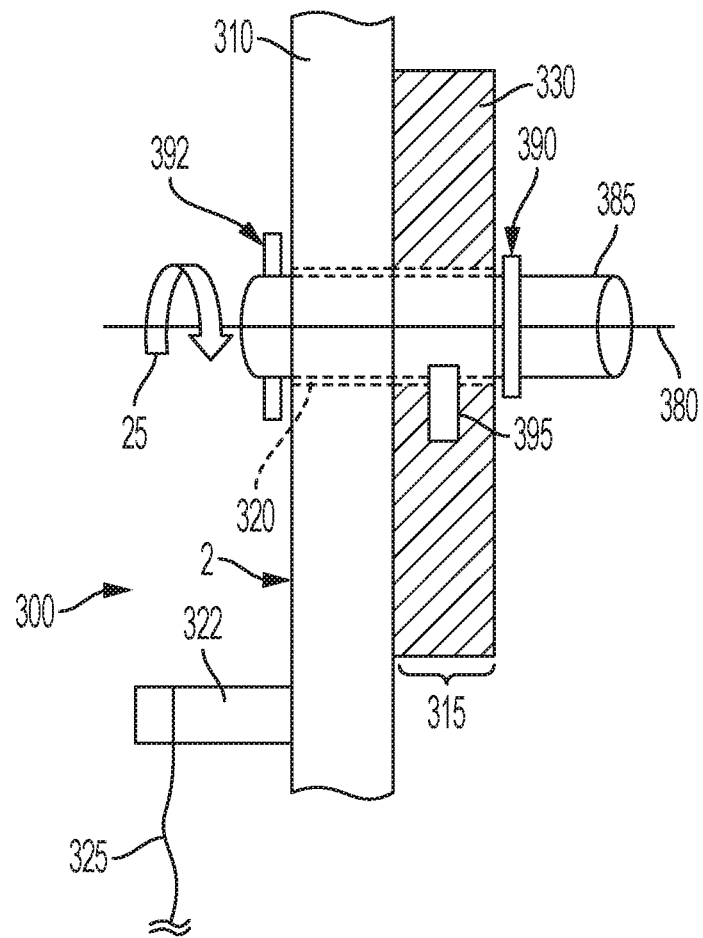
FIG. 5 illustrates an embodiment of a cam lever, according to the subject invention, operably connected to a motor shaft. Also shown is the pin on the motor shaft that engages with the step to turn the cam lever to the point of freefall.
Figure 8A:
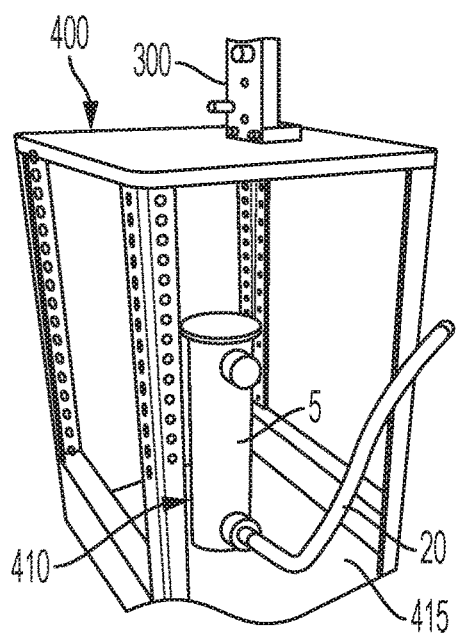
FIG. 8A shows an embodiment of a ventilator, according to the subject invention, with a mask tubing attachment and a frame in which the ventilator and motor assembly are secured.
Figure 8B:
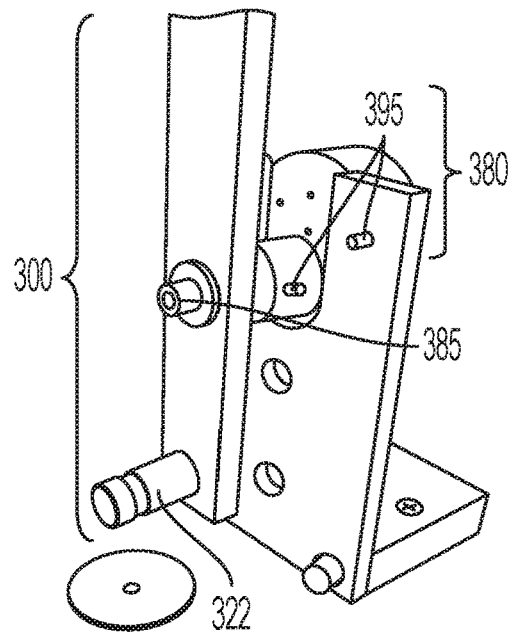
FIG. 8B shows an embodiment of the cam lever and motor assembly, according to the subject invention.

The cam lever can be positioned on the motor shaft to limit linear movement of the shaft, but not inhibit rotational movement. In one embodiment, the motor shaft has a radial shoulder 390, for example, between the cam lever 300 and the motor assembly, which aids in maintaining the position of the cam lever 300 on the motor shaft 385 (with center axis 380). A screw and washer, cotter pin, end cap, or other known apparatus (392) can be employed on the opposite side of the cam lever 300 to also maintain the position of the cam lever 300 on the motor shaft 385. FIGS. 5 and 8B illustrate examples of a cam lever 300 secured on a motor shaft 385.

Figure 4:
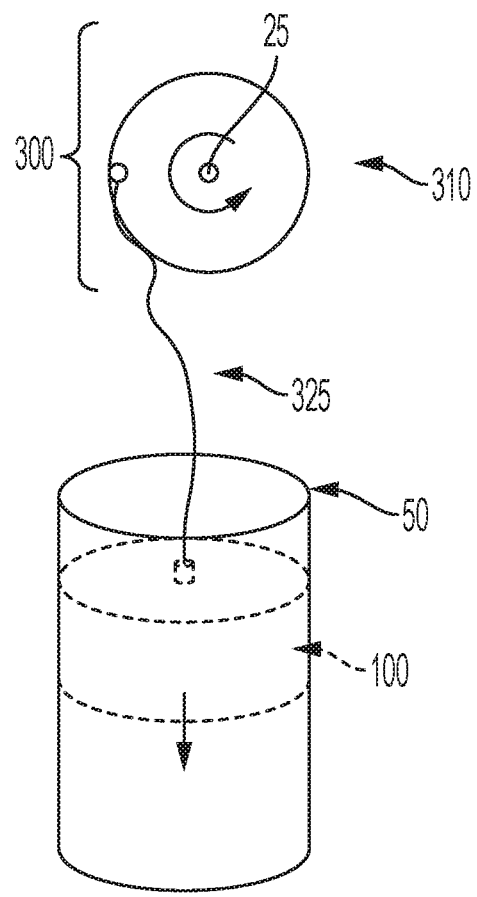
FIG. 4 is a general schematic of an embodiment of a draw cable system, according to the subject invention.

A cam lever 300 can have a crank 310, with a hub 320 there through that slides onto and freely rotates on the motor shaft 385. The flexible or semi-flexible draw cable 325 can be attached to a front face 2 of the crank and extends into the chamber, through a clearance aperture 231 in the cap 200, to operably attach to the piston 100. One example of this configuration is shown in FIGS. 2 and 4. In one embodiment, the draw cable 325 is cooperatively engaged with a crank pin 322 that cooperatively engages with the crank 310. In a further embodiment, the crank pin engages with one or more adjustment bores 323 in the crank, causing rotation 25 at different positions accordingly. Adjustment bores can be arranged on the crank in various positions, i.e., at different distances from the motor shaft, and can be used to adjust how far the draw cable is drawn up, which can dictate how much breathable air is forced out of the outlet tube 20. In an embodiment, the adjustment bores are arranged in-line at different distances (from the motor shaft) on the crank. FIG. 1 illustrates a non-limiting embodiment of a crank with a plurality of adjustment bores arranged at various distances from the central motor shaft. For example, if the crank pin is attached to an adjustment bore farther from the motor shaft (larger distance), the piston will be drawn up by the draw cable farther than it would be if the crank pin were attached to an adjustment bore closer to the motor shaft (smaller distance). This provides an advantageous ability to adjust the volume of breathable air provided to a patient for each breath.

In an embodiment, a rigid or semi-rigid draw rod 140,326 is attached to the piston to which is attached the draw cable 325 (e.g., via a draw rod eye 142). A draw rod can extend a few inches above the piston, as shown in the example in FIG. 6A, such that the draw cable 325 attaches within the chamber 50. Alternatively, the draw rod can extend from the piston and out of the clearance aperture 231 in the cap 200, as demonstrated in FIG. 2. A draw rod can align the force applied to the piston by the draw cable towards the center of the piston, which can inhibit tilting or misalignment of the piston in the chamber. In a further embodiment, a draw rod can have a weight shelf 327 outside the chamber for supporting one or more weights 175. FIG. 2 illustrates one example of a weight shelf on a draw rod with a weight thereon. This can be advantageous for quickly and easily adjusting the force applied to the breathable air in the lower portion. Weights on a weight shelf can be utilized in addition to or in place of weights placed on a piston or piston stand 150, as described above.

As mentioned above, the motor shaft 385 can be used to turn the crank 310 to a point where the crank free-falls to release the piston 100. The crank freely rotates on the motor shaft. To facilitate the motor shaft turning the crank, there can be a secondary lever system 315 that rotates the crank. In one embodiment, a secondary lever system can include a step 330 and a step pin 395. In one embodiment, a step 330 is arranged around the hub 320 on the back face 304 of the crank 322. The step can extend out from the crank and around the hub at least 180°. In a particular embodiment, the step is a "C"-shaped projection around the hub, as shown, by way of a non-limiting example in FIG. 9. Attachment of the piston 100 biases the crank in one position, usually with the adjustment bores below the hub 20. This bias can also position the step on one side, left or right, of the hub when the piston is fully descended or dropped in the chamber. Thus, in an embodiment where the step is "C"-shaped, the "C" will be to the left or right side of the hub and the adjustment bores will be below the step on the crank. In a further embodiment, the step pin 395 is arranged on the motor shaft and rotates with the motor shaft. The step pin can be further arranged on the motor shaft to engage with the step 330 during rotation. When the step pin rotates it engages at the bottom of the step, causing the crank to rotate, which raises the piston 100. As the piston is being raised, breathable air taken into the upper portion 55 through the intake tube 10 is forced into the lower portion 60 through the channels 130 in the piston, which moves the piston valve 110 to let the breathable air pass. Because the step partially surrounds the hub and the crank is biased on one end, the step pin can raise the biased end of the crank only until the step reaches a point where the biasing of the crank causes it to suddenly rotate around the motor shaft faster than the motor shaft rotates the step pin. This can result in the step disengaging from the step pin and allowing the crank to free-fall for the rest of the rotation, which also allows the piston to fall in the chamber and compress the breathable air that was forced into the lower portion. As the breathable air is compressed it is forced out of the outlet tube 10 in the lower portion to insufflate a patient. The free-falling piston will again bias the crank until the step pin rotates around to again engage with the step, raising the crank to the point where it falls and again drops the piston. This simple mechanical process can continue indefinitely until the motor assembly is turned off. FIGS. 5 and 8A illustrate examples of a cam lever arranged on a motor shaft and demonstrate how the step pin rotates to engage with the step to turn the crank and rotates to raise the piston.

It can be beneficial for the cam lever to be arranged above the chamber so as to minimize the angle at which the draw cable moves through the clearance apertures 231 in the cap 200. In one embodiment, the ventilator 5 is secured to a frame 400 that supports the motor assembly and positions the cam lever above the ventilator. FIG. 8A illustrates an example of a frame that can be used to support a motor assembly and the attached cam lever above a ventilator. In a particular embodiment, the cap 200 includes openings in which frame pins 410 can be passed to connect to the frame and secure the ventilator to the frame.

It will be appreciated that ventilators of embodiments of the subject invention can advantageously be adjusted through mechanically means to change the volume and pressure of breathable air supplied to the patient. This does not preclude the use of one or more sensor systems 500 from being utilized with a ventilator of an embodiment of the subject invention. For example, one more sensors can be employed to monitor components or pressure on the interior of the chamber 50.

Figure 10A:
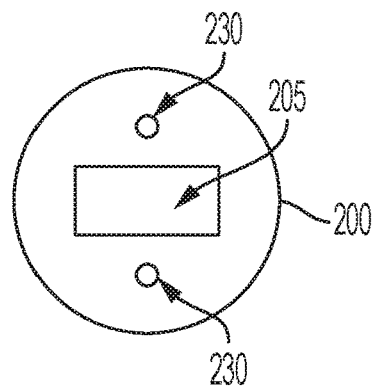
FIG. 10A illustrates an embodiment of a cap, according to the subject invention, for closing the top of a chamber. In this embodiment, the cap includes a depression for receiving a photomicrosensor to detect the position of a piston in the chamber.
Figure 11:
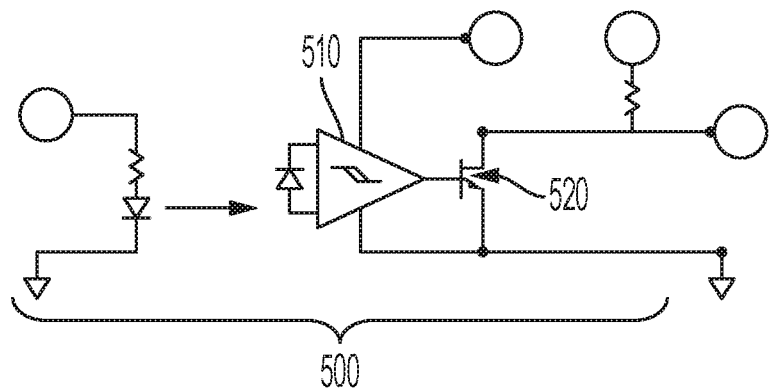
FIG. 11 is a schematic of the circuitry of a "light-on" photomicrosensor utilized with embodiments of the subject invention.

In one embodiment, an optical sensor system is arranged inside the chamber to monitor the position of the piston 100. An optical sensor system can include a phototransistor having a light source 510 and a light sensor 520, which can determine the location of the piston inside the chamber. In one embodiment, a photomicrosensor, such as, for example, an SY313 or SY413, can be mounted inside the chamber 50 to measure the distance of the piston from the cap 200. In one embodiment, the photomicrosensor is mounted in a depression 205 in the cap, as demonstrated in FIG. 10A. FIG. 11 shows one example of the wiring schematic that can utilized with an optical sensor system that includes a photomicrosensor.

Figure 16:
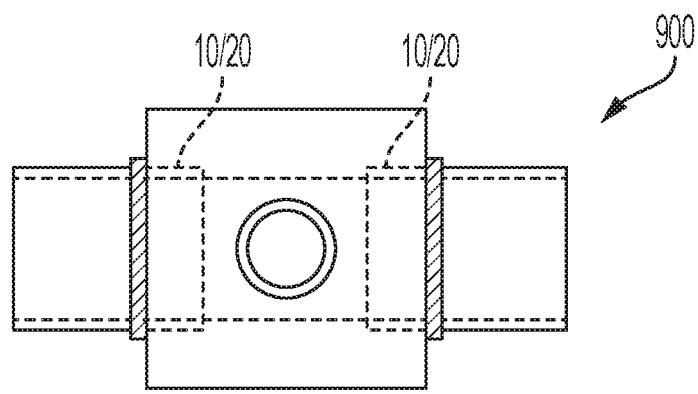
FIG. 16 illustrates a general pressure sensor that can be utilized with the ventilator embodiments of the subject invention to regulate the breathable air that enters the ventilator upper portion.

In another embodiment, one or more pressure sensors 900 can be arranged on the ventilator 5 to monitor and/or control the breathable air pressure as the ventilator operates. Pressure sensors are known in the art and are often utilized to measure air pressures. FIG. 16 illustrates one example of pressure sensor that can be used with embodiments of the subject invention. In one embodiment, there is a pressure sensor on at least one of the intake tube and the outlet tube to monitor breathable air pressure being taken into the upper portion 60 and the breathable air pressure being forced out of the outlet tube, respectively. For example, the breathable air pressure can be measured and, if necessary, adjusted prior to the ventilator being used on a patient. As the ventilator operates, breathable air pressure can be monitored to ensure that a sufficient volume of breathable air, at the appropriate pressure, is delivered to the patient.

As described above, ventilators of embodiments of the subject invention can advantageously be adjusted to increase the volume and pressure of air delivered to a patient. A ventilator can also be advantageously adjusted to increase the speed at which breathable air is moved through the ventilator. By increasing the rotation speed (e.g., rotations per minute (rpm)) of the motor shaft, the piston can be raised and released at a faster rate. This could allow a ventilator to supply breathable air to more than one patient. In one embodiment, the components of a ventilator, as described above, are adjusted so as to increase the rate of breathable air sufficiently to assist at least two patients.

The ability to provide a volume of breathable air to two patients necessitates that the outlet tube 20 be modified to direct the breathable air to each patient. One option is to bifurcate the outlet tube that leads to the patient and adjust the volume and pressure so that sufficient breathable air is delivered to the bifurcated tubes and the patients. Another option is to use a valve to direct breathable air to one patient at a time. The ventilator speed can be adjusted so that during each cycle one patient is insufflated, while the other patient is exhaling and the process reverses for the next cycle. This can provide sufficient breathable air to properly insufflate one patient while the other patient exhales.

Figure 12A:
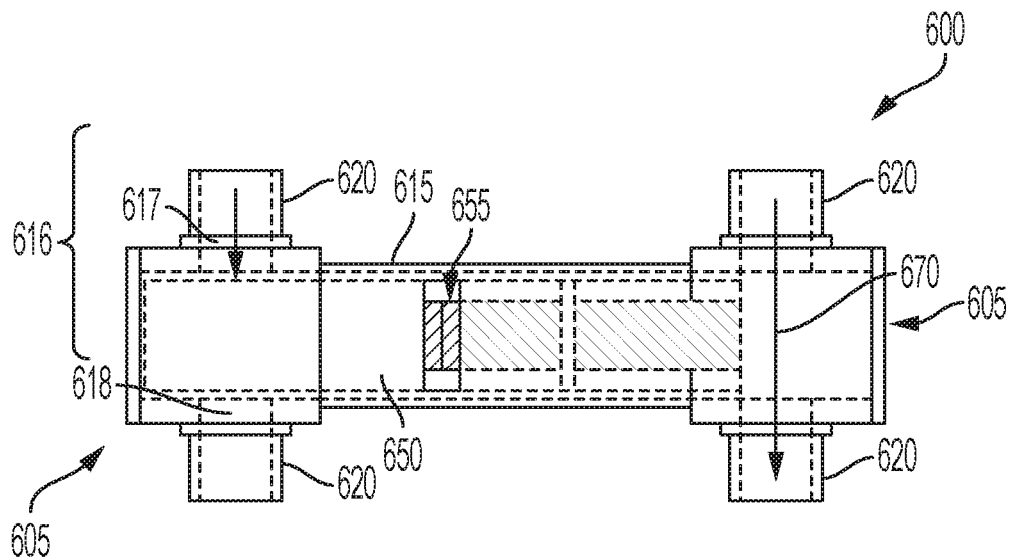
FIGS. 12A and 12B illustrate embodiments of a shuttle valve, according to the subject invention, which alternates the output of a ventilator of the subject invention to provide breathable air to two patients.
Figure 12B:
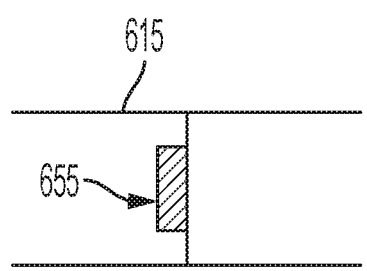
Figure 19A:
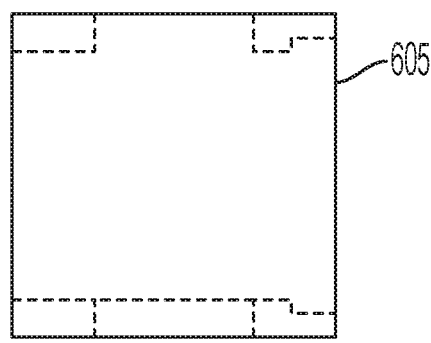
FIGS. 19A, 19B, and 19C show views of an end cap, according to an embodiment of the subject invention, which can be used to close the ends of a shuttle valve.
Figure 19B:
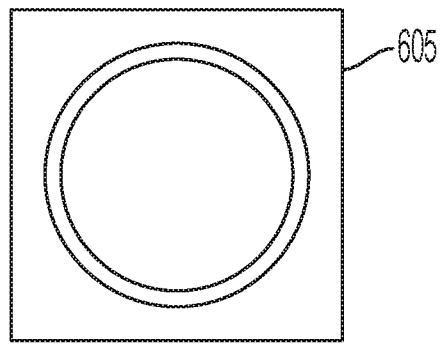
Figure 19C:
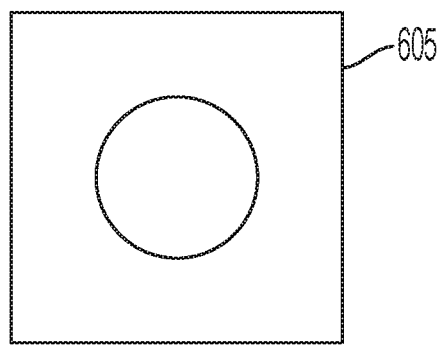
Figure 20:
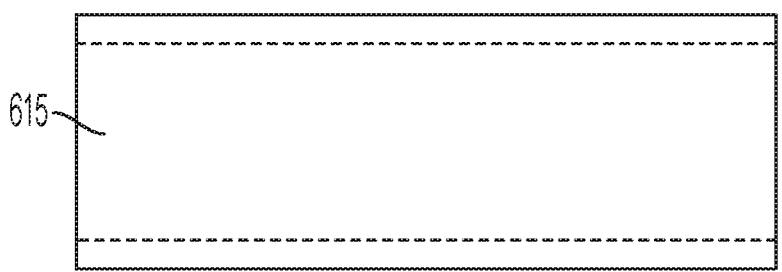
FIG. 20 illustrates an embodiment of a shuttle tube, according to the subject invention.
Figure 21:
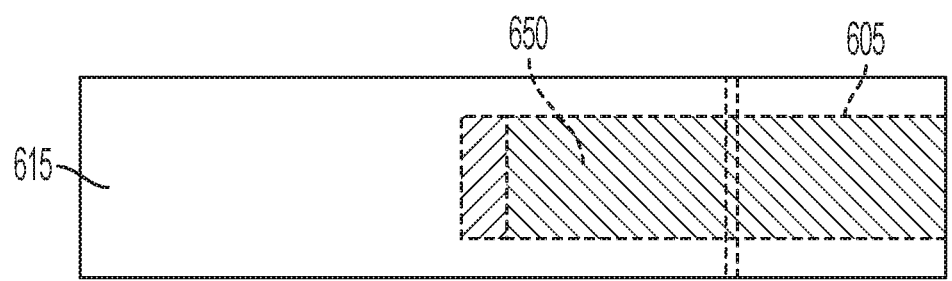
FIG. 21 illustrates embodiments of a shuttle tube and captive piston thereon, according to the subject invention.
Figure 22:
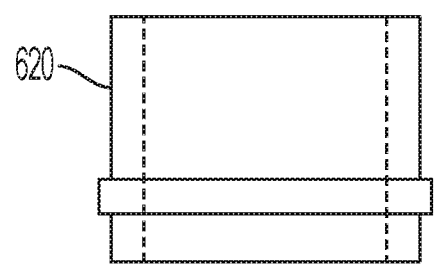
FIG. 22 illustrates an embodiment of a hose stub, according to the subject invention, which can be affixed to a paired port in a shuttle valve.

In one embodiment, a shuttle valve 600 is operably connected between the outlet tube 20 and the patients. A shuttle valve can switch the breathable air between two patients. In one embodiment, a shuttle valve is a tubular construct, such as shown in FIG. 20, which comprises a shuttle tube 615 with a captive piston 650 slidably retained therein. FIG. 21 demonstrates a captive piston within a shuttle tube. Each end of the shuttle tube is sealed, such as, for example, with an end cap 605 that also allows access to the captive piston. FIGS. 19A, 19B, and 19C illustrate one example of an end cap. Also at each end of the shuttle tube are paired ports 616 that include an inspiration port 617, leading to a patient and a breathable air port 618 that comes from the ventilator. The paired ports provide a passageway 670 that is perpendicular to the shuttle tube. The captive piston can slide to each end of the shuttle tube. When the captive piston slides to one end, the paired ports at that end are blocked to close the passageway. The paired ports at the opposite end are not blocked and the passageway is open to allow breathable air to pass through the shuttle tube. FIG. 12 illustrates one example of a shuttle valve. The breathing apparatus attached to the patients can be attached to the inspiration ports of the paired ports. The ventilator outlet tube can be operably connected to the breathable air ports. The ventilator can be adjusted accordingly to provide a volume of breathable air at a rate necessary to assist each patient as the captive piston slides through the shuttle tube. To assist with attachment to the pair ports, one or more hose stubs 620 can be operably connected to the ports. FIG. 22 illustrates one example of a type of hose stub 620 that can be utilized with one or more of the paired ports.

The captive piston 650 can be moved at regular, predetermined intervals within the shuttle tube 615 to facilitate delivery of breathable air to both patients operably connected to the ventilator 5. Ventilators of embodiments of the subject invention can be utilized with one or two patients. Thus, it can be beneficial if the captive piston can be retained towards one end of the shuttle tube, if it is necessary that breathable air be supplied to a single patient. In one embodiment, the position of the captive piston is regulated externally to the shuttle tube. In a further embodiment, the position of the captive piston is passively regulated.

Figure 13:
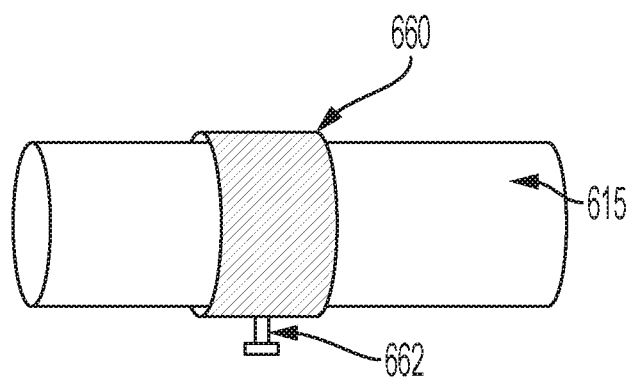
FIG. 13 illustrates an embodiment of a shuttle ring, according to the subject invention, that can be used to alternate the position of a captive piston to open and close vents in shuttle valve.

In one embodiment, the captive piston 650 has a magnet 655 fixedly attached thereto. The magnet can be fixedly attached at or about the center of the captive piston. Preferably, the magnet has sufficient force to penetrate the shuttle tube. In a further embodiment, there is a slidable metal actuator 660 in proximity to the exterior of the shuttle tube. In a specific embodiment, the metal actuator at least partially surrounds the shuttle tube 615. FIG. 13 illustrates a non-limiting example of metal actuator. The proximity of the metal actuator and magnet creates a magnetic field, such that when the metal actuator is moved along the exterior of the shuttle tube, the magnet on the captive piston follows sliding the captive piston within the shuttle tube. Thus, the metal actuator can slide the captive piston to one or the other end of the shuttle tube. It will be understood by a person of skill in the art that embodiments of the subject invention are not limited by the position of the magnet and the metal actuator. The metal actuator and magnet could be just as easily reversed to achieve the same effect of sliding the captive piston within the shuttle tube.

As discussed above, the passageways 670 in the shuttle tube 615 are preferably opened and closed at regular, pre-determined intervals to provide breathable air to a patient at likewise regular, pre-determined intervals. In one embodiment, the metal actuator 660 is connected to an electronically controlled and timed shuttle lever 700. The motion of the shuttle lever can move the actuator along or on the shuttle tube to effect movement of the magnet 655 on the piston. In one embodiment, the shuttle lever is configured with a pivot point 720 that allows a first end 702 of the shuttle lever to rock back and forth via the pivot point 720 between the ends of the shuttle tube 615. The metal actuator can also have a cam nut 662 slidable captured within a slot 710 so that as the first end rotates the metal actuator 660 can maintain proximity to the magnet 655 on the captive piston 650.

Figure 14:
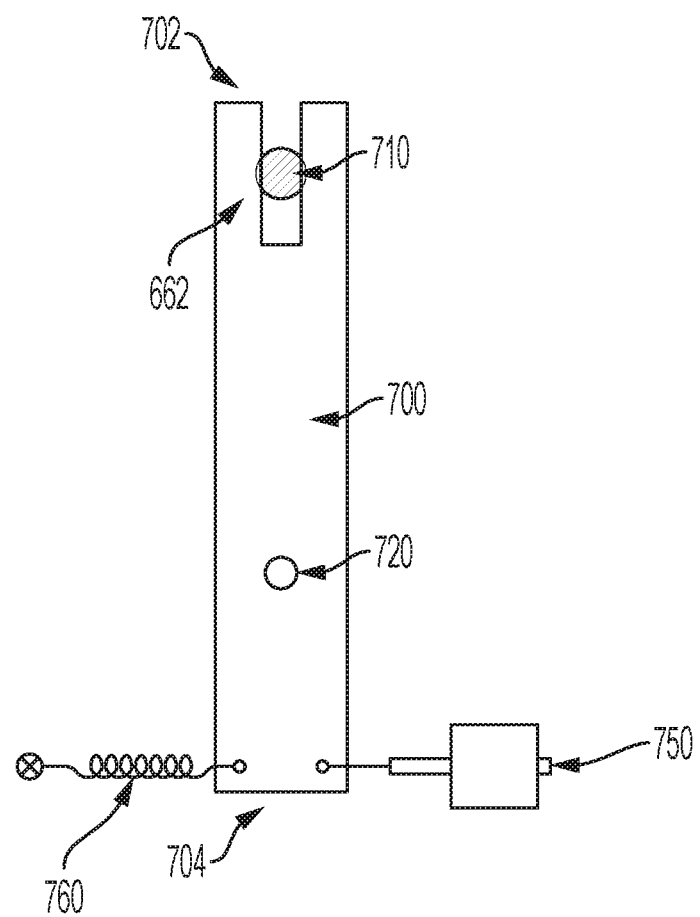
FIG. 14 illustrates an embodiment of a shuttle lever, according to the subject invention, that can be used to move a shuttle ring.

The rocking motion of the shuttle lever 700 on the pivot point can be directed by any of a variety of electronic mechanisms. In one embodiment, the second end 704 of the shuttle lever 700 is operably connected to a solenoid mechanism 750 and a return spring 760. The solenoid mechanism can pull the second end of the shuttle lever so that the first end moves in the opposite direction, thereby moving the captive piston and magnet to one end of the shuttle tube. This can block the paired port 617 at that end and the passageway 670. After a predetermined time the solenoid can release the shuttle lever. The return spring can pull the second end of the shuttle lever in the opposite direction as the solenoid. When the solenoid releases the second end, the spring pulls the second end back to the starting position, which causes the first end 702 to move to the opposite end of the shuttle tube, thereby blocking the other pair ports. This cycle can be repeated to regularly provide two patients with breathable air. FIG. 14 demonstrates the operation of an embodiment of a shuttle lever.

Figure 15:
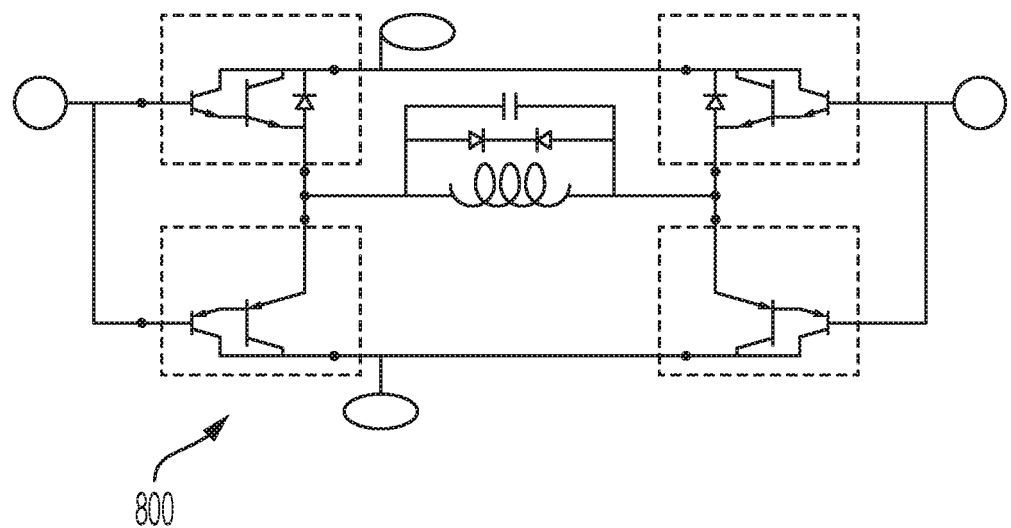
FIG. 15 illustrates an embodiment of a coil driver, according to the subject invention, employed to move the shuttle ring, as an alternative to the shuttle lever.

In an alternative embodiment, two solenoids can be attached to the second end of the shuttle lever and configured to push and pull the second end so that slide the piston in the shuttle tube. This is not shown in the figures, but would be readily understood by a person of skill in the art. In yet a further embodiment, a paired electromagnetic coil driver 800 system can be arranged on or near the shuttle tube. With this embodiment, an electromagnetic coil can be arranged at each end of the shuttle tube that can pull the magnet on the captive piston to each end of the shuttle tube. By alternating the on/off of the electromagnetic coils, the passageways can be opened at pre-determined intervals. FIG. 15 illustrates a non-limiting example of an electromagnetic coil system that could be used with shuttle valve embodiments of the subject invention.

Figure 10B:
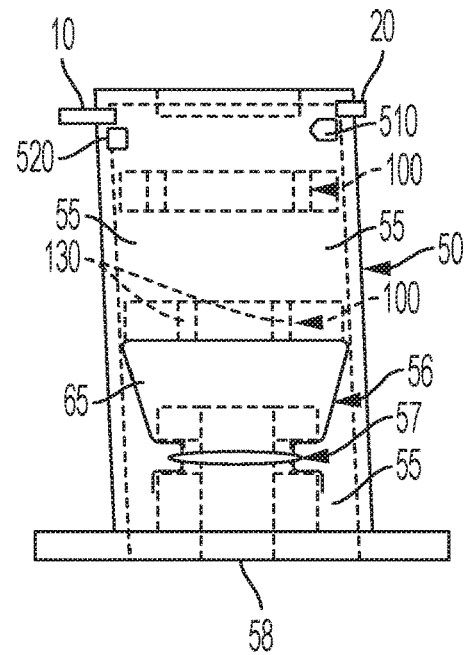
FIG. 10B illustrates an alternative embodiment of a ventilator, according to the subject invention, which utilizes an internal bladder to raise a piston that subsequently deflates the bladder to force breathable air into the lungs of a patient.

In alternative embodiments, a ventilator 5 can utilize a different mechanism for raising and releasing a piston 100. In an embodiment, an example of which is illustrated in FIGS. 10A and 10B, a bladder 65 can be employed to raise the piston 100 to a pre-determined or pre-calibrated height in the chamber 50. Breathable air is taken into the upper portion 60 through the intake tube and is also pushed out of the upper portion through an outlet tube 20 arranged in the upper portion. The bladder can be sealably attached to a nipple 56 on the bottom interior of the chamber 50, such as shown, for example, in FIG. 18. For example, an O-ring can secure the open end of the bladder around the nipple and press the bag material into a groove 57 that seals the bladder around the nipple and secures the O-ring in place. The nipple can lead to a pump port 58 in which air can be pumped to inflate the bladder. The piston can be supported by the bladder and can operate to deflate the bladder during each cycle.

Breathable air can be pumped into the upper portion, as described above. Simultaneously or following the upper portion being filled with breathable air, the bladder is filled with air as well, which raises the piston upwards and towards the upper portion 60. This increases the pressure in the upper portion and forces the breathable air through the outlet tube 20 to the patient. When the pressure in the upper portion decreases to a specific point, the bladder is no longer filled and the weight of the piston thereon causes the bladder to be compressed and retract downward in the chamber. As the next cycle begins the upper portion is filled with breathable air, the bladder is filled with air to raise the piston, the breathable air is compressed and pushed out of the outlet tube, the bladder stops filling, the piston compresses the bladder, and the cycle repeats.

In one embodiment, a pressure sensor 900 can be operably connected to one or more of the intake port 10, outlet port 20, and pump port 58 to measure and/or regulate any of these pressures. In a further embodiment, one more sensor systems 500 can be utilized to monitor the position of the piston within the chamber. In a particular embodiment, a sensor system is arranged in the chamber and is triggered when the piston is raised to the level of the sensor system. For example, an optical sensor system can be utilized to detect when the piston is raised to just below the outlet tube.

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1: Gravity-Dependent Ventilator for Providing a Volume of Breathable Air to a Patient One embodiment of the ventilator is shown in FIG. 1. It has the following characteristics:

1) 13" long hollow cylinder or longer as the chamber. This hollow cylinder has an inner dimension of 3" and is long enough to allow for 0.5 liters of volume displacement during movement.
2) Clearance fit (0.005" clearance) piston, 0.5 lb in weight and adjustable for heavier load, with several channels to allow oxygen mixture to flow when the piston valve is open.
3) Cap at the top of the cylinder with several vents for air flow when the cap valve is open.
4) Motor assembly at 20 RPM rotation speed and >10 ft-lb torque. The motor assembly is equipped with a cam lever connected to a draw cable that is also attached to a PTFE piston on the other side. The draw cable serves to move the piston up and down as the motor rotates the cam lever.
5) Intake oxygen tube at the top of the cylinder, possibly from a humidifying device, and an output tube at the bottom of the cylinder connected to the patient mask.
6) External frame for stabilizing the ventilator. Two long metal frame pins can be mounted through the cap and bolted to the base 415 of the frame. These frame pins serve to hold the cylinder secure. The motor assembly is also placed on and secured to the top of the frame.
7) A cap valve placed at the top of cap, outside the ventilator, that closes the 3" inner diameter cylinder and piston valve placed at the bottom surface of the piston operate to control movement of breathable air in the cylinder.
8) The piston valve is a simple captive flat film membrane fastened (e.g., with fasteners 115) to the piston on the center axis 30. It is nominally 2.75" to 2.9" in diameter, and nominally 5/1000" to 10/1000" (5 to 10 mils) thick. The piston valve membrane can be cut from a viewgraph or plastic paper jacket or extremely thin stainless steel shim stock. This piston valve membrane serves as an air valve to close and open air flow through the channels in the piston.
9) The cap valve is 3" in diameter fabricated of material such that the weight of the disk divided by the total area of the vents beneath (2 square inches) is equal to 0.022 pounds/square inches (0.125" thick delrin sheet). This cap valve seals the upper portion of the cylinder above the piston unless the pressure from the oxygen-air mix is greater than 0.022 psi. At that time, it will vent excess pressure to the ambient environment to avoid potential barotrauma to the patient.
10) The piston is an important element. The piston's weight divided by the cross-sectional area of the cylinder determines the pressure output to the patient. Therefore, there is no possibility of causing excessive pressure. It is fully gravity dependent as the piston mass multiplied by the acceleration due to gravity determines the pressure. Note that in this embodiment there is no draw rod that goes through the clearance aperture in the cap only a draw cable that connects the crank of the cam lever above to the piston.
11) The top of the piston has draw rod with an axial eye extending upwards for several inches, but remains within the cylinder. This is the draw rod, attached to the draw cable, used to pull the piston up. The stand extending up at the top of the piston allows for additional mass or weights to be placed on the top of the piston. This weight can be 2" in diameter at the bottom and can step up to 2.5" in diameter when it is 0.5" from the end. This creates a clearance step to allow for air flow through the piston channels. The weights are slotted from the edge to the tapered seat and can therefore be slipped over the cable and draw rod.
12) The cam lever above the cylinder is placed far enough above the cap to allow free rotation and, therefore, minimize the cable's angular displacements during each cycle.
13) The cam lever comprises a hub which freely rotates on the motor's shaft with an attached crank arm.
14) The arm is made captive through the use of a shoulder on the drive shaft, a screw and washer assembly on the drive shaft's axis of rotation.
15) A step protrudes outward for some distance from the crank around the hub. This step is aligned at the same angle as the draw cable arm.
16) The drive shaft has a step pin that extends out in one direction (radial but not extending through both sides) to engage the step on the free-rotating cam lever.
17) As the drive shaft rotates, the step pin engages the step around the hub at the bottom of the stroke and causes the step to rotate upwards until the crank passes top-dead-center position. Once the crank passes top-dead-center, it then freely falls to the starting position, which releases the piston and compressing the breathable air in the cylinder as the piston free-falls to the bottom of the stroke.
18) The crank remains in this position until the step pin catches up with the step around the hub again. This is repeated, once again, when it is pulled upward. The latter stroke refills the breathable air in the lower portion with the breathable air that was sucked into the top chamber during the piston's fall and prepares it for the next compression cycle.
19) The location of the connection of the draw-cable to the crank dictates the volumetric stroke. The stroke length is determined at twice the distance from the crank's rotational axis to the connection point for the draw-cable. The distance "R" from the hub's center of rotation to the connection point volume dependence is as follows:
    a. R=1 inch=>Volume=0.232 liters
    b. R=1.5 inch=>Volume=0.347 liters
    c. R=2 inches=>Volume=0.464 liters
    d. R=2.16 inches=>Volume is 0.5 liters
    e. R=2.5 inches=>Volume=0.579 liters
    f. R=3 inches=>Volume=0.695 liters
20) By placing several attachment points at different distances on the arm, the volume delivered is easily set and visually confirmed.

Example 2: Operation of the Gravity-Dependent Ventilator

In one embodiment, the operation of the ventilator is as follows:

1) As the cam lever rotates, the piston moves up and down.
2) Prior to the rotation, the cap valve on the top of the cap is open and the piston valve at the bottom surface of the piston is also open. In this mode (all valves open), the intake valve fills the upper portion (volume above the piston) with breathable air.
3) When the piston is released and moves down, the cap and piston valves serve to close the vents and channels in the cap and piston, respectively. This is done passively via air pressure created as the piston falls in the cylinder. As the piston moves downward, air pressure allows for breathable air, which can include additional oxygen, to be pushed through the outlet tube and into the nozzle connected to the patient mask.
4) As the motor continues to rotate, the piston is raised by the motor, which again causes the piston valve to open to fill the lower portion with the breathable air/oxygen mixture that was taken into the upper portion as or soon after the piston previously fell. As the breathable air/oxygen are pulled into the lower portion through the channels in the piston, the cap valve can open if the air pressure in the upper portion raises above a set pressure.
5) The above operation is repeated as the motor continues to make another 360° rotation.

Example 3: Pressure Sensitivity Setting Mechanism

The pressure at which the breathable air is pushed into the outlet tube is determined by the pressure applied to the breathable in the lower portion by the piston. This pressure is set by the weight of the piston divided by the radial cross-sectional area of the cylindrical chamber in which the piston slidable moves. The area of a 25 mm in diameter cylinder is 0.76 square inches. A 5 mm thick PTFE piston (about 0.5 grams of mass or 0.012 pounds of weight) riding in this bore would give a pressure of 0.015 PSI to move upwards. If the piston was a cup only 0.5 mm thick in the center with 5 mm high walls 1 mm thick this would give an activation pressure of 0.003 PSI.

Typical minimum supply pressures are 5 cm of $H_2O$ or 0.07 PSI. An activation pressure of 0.015 PSI is 22% of that value and should be fine, particularly at supply pressures of 30 cm of $H_2O$ or 0.42 PSI.

Example 4: Description of a Sensor System for Use with an Embodiment of a Bladder Operated Ventilator 1. The bladder is initially deflated and the piston collapsed thereon is out of sensing range of a SY313/SY413 photomicrosensor. At this time, the photomicrosensor is in State 0.
2. The ventilator begins to supply breathable air to a patient through an outlet tube in a switch body. The bladder begins to inflate and lift the piston. The piston rises on the bladder until it comes within detection range of the SY313/SY413 photomicrosensor, which goes to State 1. The photomicrosensor remains in State 1 until the ventilator pulse has ended. This pulse duration is designated $T_c$ and is typically about 3 seconds.
3. The transition between the States generates a rising or falling edge step on the output of the photomicrosensor. This voltage is passed to a 74LS123 monostable multivibrator. The 74LS123 is triggered and supplies a pulse of duration $T_w \ll T_c$, where $T_w = 0.001$ seconds).
4. This pulse is fed into the Internal Clock (IC) inputs of a dual JK flip flop set to "Toggle" states. The 2 flip flops on the IC are wired in parallel to increase the output handling capability of the circuit. It not usually necessary that they be arranged parallel, but it is not problematic to do so
5. The flip flop output goes to Q "high" (nominally above 3.5 volts) and NotQ "low" (nominally below 1.5 volts). Flip Flop is in State A and will remain there until it receives another pulse from the 74LS123.
6. The Q and NotQ outputs from the flip flop drive the power switching stage to drive one of the 2 solenoids, or alternatively, a single coil where the current flow reverses depending on the Q and NotQ values. The Flip Flop is still in State A.
7. When the ventilator pulse ends, the piston collapses the bladder to below the SY313/SY413 sensing distance and the sensor state goes back to where it was initially. The Flip Flop is still in State A.
8. The ventilator again begins to supply breathable air to the patient through outlet tube in the switch body. The bladder begins to inflate and lifts the piston. The piston again comes within detection range of the SY313/SY413 photomicrosensor, which goes into State 1. The sensor remains in State 1 until the ventilator pulse is ended.
9. The transition between the States generates a rising or falling edge step on the output of the sensor. This voltage is sent to the 74LS123 monostable multivibrator. The 74LS123 is triggered and supplies a pulse of duration $T_w \ll T_c$, which is about $T_w = 0.001$ seconds.
10. This pulse is fed into the Interal Clock (IC) inputs of a dual JK flip flop set to "Toggle" states. The 2 flip flops on the IC are wired in parallel to increase the output handling capability of the circuit. Again, it not required that the 2 flip flops be wired in parallel.
11. The flip flop output goes to Q "low" (nominally below 1.5 volts) and NotQ "high" (nominally above 3.5 volts). Flip Flop is now in State B and will remain in that State until it receives another pulse from the 74LS123.
12. The Q and NotQ outputs from the flip flop drive the power switching stage to drive either 2 solenoids or a single coil where the current flow reverses depending on the Q and NotQ values. Flip Flop is still in State B.
13. The ventilator pulse ends. The piston collapses the bladder to below the SY313/SY413 sensing distance and the sensor state returns to the initial State. Flip Flop is still in State B1.
14. At this point the ventilator has completed two cycles and each output "A" or "B" has received one of the ventilator's output pulses.
15. The process is repeated starting at step 1 above.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:
1. A ventilator, comprising:
    a chamber having a closed bottom, a sidewall, a top opposite from the bottom in an axial direction;
    a cap covering the top of the chamber;
    a piston disposed in an interior of the chamber, in contact with the sidewall of the chamber, and dividing the interior of the chamber into an upper portion between the piston and the cap and a lower portion between the piston and the bottom of the chamber;
    an inlet configured to provide air into the upper portion of the chamber;
    an outlet configured to evacuate air from the bottom portion of the chamber; and
    a driving element operably connected to the piston and configured to move the piston upwards towards the top of the chamber in the axial direction, the piston comprising at least one piston channel therethrough, the piston further comprising a passive piston valve on the at least one piston channel and configured to allow air to flow through the at least one piston channel from the upper portion of the chamber to the lower portion of the chamber while inhibiting air from flowing through the at least one piston channel from the lower portion of the chamber to the upper portion of the chamber, the cap comprising at least one vent therethrough, the cap further comprising a passive cap valve on the at least one vent and configured to allow air to flow through the at least one vent from the upper portion of the chamber to an outside of the chamber while inhibiting air from flowing through the at least one vent from the outside of the chamber to the upper portion of the chamber, the driving element comprising a motor, and the piston having a mass that is large enough such that the piston, when not being moved upwards or inhibited from moving downwards by the driving element, overcomes friction with the sidewall of the chamber to move downwards towards the bottom of the chamber due to gravity.

2. The ventilator according to claim 1, the passive piston valve comprising a first membrane on a bottom face of the piston that faces the bottom of the chamber.

3. The ventilator according to claim 2, the passive cap valve comprising a second membrane on a top face of the cap that faces the outside of the chamber.

4. The ventilator according to claim 1, the passive cap valve comprising a second membrane on a top face of the cap that faces the outside of the chamber.

5. The ventilator according to claim 1, the motor comprising a motor shaft and a motor element configured to rotate the motor shaft, the driving element further comprising:
a cam lever connected to the motor shaft;
a cam pin connected to the cam lever; and
a draw cable connected to the cam pin and the piston,
the driving element being configured to move the piston upwards by a turning of the cam lever together with the rotating of the motor shaft, causing the cam pin to move upwards and pull the piston upwards via the draw cable, and
the driving element allowing the piston to move downwards due to gravity when the cam pin is not moving upwards.

6. The ventilator according to claim 5, the driving element further comprising a cam lever step connected to the cam lever and a motor shaft pin on the motor shaft, and the motor shaft pin being configured to engage the cam lever step as the motor shaft rotates, causing the cam lever to turn together with the motor shaft.

7. The ventilator according to claim 5, the cam lever comprising a plurality of adjustment bores at different distances from the motor shaft, each adjustment bore of the plurality of adjustment bores being configured to receive the cam pin.

8. The ventilator according to claim 1, the chamber being a cylinder, the piston having a circular cross-section, taken in a horizontal direction perpendicular to the axial direction, and
the cap having a circular cross-section taken in the horizontal direction.

9. The ventilator according to claim 8, the piston having a variable radius through its thickness, such that an uppermost portion of the piston and a lowermost portion of the piston are in contact with the sidewall of the chamber while an intermediate portion of the piston between the uppermost portion and the lowermost portion is spaced apart from the sidewall of the chamber.

10. The ventilator according to claim 1, the motor being an electric motor, and the motor being the only electric element of the ventilator or in operable communication with the ventilator.

11. A method of providing ventilation to a patient in need of ventilation a ventilator that comprises:

a chamber having a closed bottom, a sidewall, a top opposite from the bottom in an axial direction;
a cap covering the top of the chamber;
a piston disposed in an interior of the chamber, in contact with the sidewall of the chamber, and dividing the interior of the chamber into an upper portion between the piston and the cap and a lower portion between the piston and the bottom of the chamber;
an inlet configured to provide air into the upper portion of the chamber;
an outlet configured to evacuate air from the bottom portion of the chamber; and
a driving element operably connected to the piston and configured to move the piston upwards towards the top of the chamber in the axial direction,
the piston comprising at least one piston channel therethrough,
the piston further comprising a passive piston valve on the at least one piston channel and configured to allow air to flow through the at least one piston channel from the upper portion of the chamber to the lower portion of the chamber while inhibiting air from flowing through the at least one piston channel from the lower portion of the chamber to the upper portion of the chamber,
the cap comprising at least one vent therethrough,
the cap further comprising a passive cap valve on the at least one vent and configured to allow air to flow through the at least one vent from the upper portion of the chamber to an outside of the chamber while inhibiting air from flowing through the at least one vent from the outside of the chamber to the upper portion of the chamber,
the driving element comprising a motor, and
the piston having a mass that is large enough such that the piston, when not being moved upwards or inhibited from moving downwards by the driving element, overcomes friction with the sidewall of the chamber to move downwards towards the bottom of the chamber due to gravity, the method comprising:
connecting the outlet to the patient;
providing breathable air to the upper portion of the chamber via the inlet; and
operating the motor so that the piston is cyclically and repeatedly pulled upwards and then allowed to fall downwards due to its mass, forcing air from the upper portion of the chamber to the lower portion of the chamber through the at least one piston channel during the upwards movement and pushing air out of the lower portion via the outlet and to the patient during the downwards falling.

12. The method according to claim 11, the passive piston valve comprising a first membrane on a bottom face of the piston that faces the bottom of the chamber, and the passive cap valve comprising a second membrane on a top face of the cap that faces the outside of the chamber.

13. The method according to claim 11, the motor comprising a motor shaft and a motor element configured to rotate the motor shaft,
the driving element further comprising:
a cam lever connected to the motor shaft;
a cam pin connected to the cam lever; and
a draw cable connected to the cam pin and the piston,
the operating of the motor comprising rotating the motor shaft so that the cam lever turns, causing the cam pin to move upwards and pull the piston upwards via the draw cable, and
the piston being allowed to fall downwards due to gravity when the cam pin is not moving upwards.

14. The ventilator according to claim 13, the cam lever comprising a plurality of adjustment bores at different distances from the motor shaft, each adjustment bore of the plurality of adjustment bores being configured to receive the cam pin.

15. The method according to claim 11, the chamber being a cylinder,
the piston having a circular cross-section, taken in a horizontal direction perpendicular to the axial direction,
the cap having a circular cross-section taken in the horizontal direction, and
the piston having a variable radius through its thickness, such that an uppermost portion of the piston and a lowermost portion of the piston are in contact with the sidewall of the chamber while an intermediate portion of the piston between the uppermost portion and the lowermost portion is spaced apart from the sidewall of the chamber.

16. The method according to claim 11, the motor being an electric motor, and
the motor being the only electric element of the ventilator or in operable communication with the ventilator.

17. A ventilator, comprising:
a chamber having a closed bottom, a sidewall, a top opposite from the bottom in an axial direction;
a cap covering the top of the chamber;
a piston disposed in an interior of the chamber, in contact with the sidewall of the chamber, and dividing the interior of the chamber into an upper portion between the piston and the cap and a lower portion between the piston and the bottom of the chamber;
an inlet configured to provide air into the upper portion of the chamber;
an outlet configured to evacuate air from the bottom portion of the chamber; and
a driving element operably connected to the piston and configured to move the piston upwards towards the top of the chamber in the axial direction,
the piston comprising at least one piston channel therethrough,
the piston further comprising a passive piston valve on the at least one piston channel and configured to allow air to flow through the at least one piston channel from the upper portion of the chamber to the lower portion of the chamber while inhibiting air from flowing through the at least one piston channel from the lower portion of the chamber to the upper portion of the chamber,
the cap comprising at least one vent therethrough,
the cap further comprising a passive cap valve on the at least one vent and configured to allow air to flow through the at least one vent from the upper portion of the chamber to an outside of the chamber while inhibiting air from flowing through the at least one vent from the outside of the chamber to the upper portion of the chamber,
the driving element comprising a motor,
the piston having a mass that is large enough such that the piston, when not being moved upwards or inhibited from moving downwards by the driving element, overcomes friction with the sidewall of the chamber to move downwards towards the bottom of the chamber due to gravity,
the passive piston valve comprising a first membrane on a bottom face of the piston that faces the bottom of the chamber,
the passive cap valve comprising a second membrane on a top face of the cap that faces the outside of the chamber,
the motor comprising a motor shaft and a motor element configured to rotate the motor shaft,
the driving element further comprising:
a cam lever connected to the motor shaft;
a cam pin connected to the cam lever;
a draw cable connected to the cam pin and the piston;
a cam lever step connected to the cam lever; and
a motor shaft pin on the motor shaft,
the driving element being configured to move the piston upwards by a turning of the cam lever together with the rotating of the motor shaft, causing the cam pin to move upwards and pull the piston upwards via the draw cable,
the driving element allowing the piston to move downwards due to gravity when the cam pin is not moving upwards,
the motor shaft pin being configured to engage the cam lever step as the motor shaft rotates, causing the cam lever to turn together with the motor shaft,
the cam lever comprising a plurality of adjustment bores at different distances from the motor shaft, each adjustment bore of the plurality of adjustment bores being configured to receive the cam pin,
the chamber being a cylinder,
the piston having a circular cross-section, taken in a horizontal direction perpendicular to the axial direction,
the cap having a circular cross-section taken in the horizontal direction,
the piston having a variable radius through its thickness, such that an uppermost portion of the piston and a lowermost portion of the piston are in contact with the sidewall of the chamber while an intermediate portion of the piston between the uppermost portion and the lowermost portion is spaced apart from the sidewall of the chamber,
the motor being an electric motor, and
the motor being the only electric element of the ventilator or in operable communication with the ventilator.

18. A gravity-assisted ventilator, comprising:
a chamber;
an input port coupled to the chamber;
an output port coupled to the chamber;
a weighted piston movably located in the chamber between the input port and the output port, the weighted piston including a top surface, a bottom surface, and at least one cavity passing through the weighted piston from the top surface to the bottom surface creating a piston channel;

a first passive valve coupled to the bottom surface of the weighted piston; and a motor mechanically coupled to the weighted piston allowing for the weighted piston to be lifted and dropped within the chamber between the input port and the output port.

19. The ventilator according to claim 18, the weighted piston dividing an interior of the chamber into an upper cavity and a lower cavity, the ventilator being configured such that the top surface of the weighted piston and the bottom surface of the weighted piston are both perpendicular to a gravity direction, and the weighted piston drops within the chamber with assistance of gravity, and the ventilator being further configured such that as the weighted piston drops it causes a volume of air in the lower cavity to evacuate out of the output port.

20. The ventilator according to claim 18, further comprising:

a cap covering a top of the chamber and having at least one vent passing through the cap; and a second passive valve coupled to cap.

* * * * *